(12) United States Patent
Schellenberg

(10) Patent No.: US 8,340,741 B2
(45) Date of Patent: Dec. 25, 2012

(54) SYSTEM AND MICRO-CATHETER DEVICES FOR MEDICAL IMAGING OF THE BREAST

(76) Inventor: James Schellenberg, Manitoba (CA)

( * ) Notice: Subject to any disclaimer, the term of this patent is extended or adjusted under 35 U.S.C. 154(b) by 268 days.

(21) Appl. No.: 11/570,110

(22) PCT Filed: Jun. 7, 2005

(86) PCT No.: PCT/CA2005/000881
§ 371 (c)(1),
(2), (4) Date: May 14, 2007

(87) PCT Pub. No.: WO2005/120150
PCT Pub. Date: Dec. 22, 2005

(65) Prior Publication Data
US 2007/0270635 A1    Nov. 22, 2007

Related U.S. Application Data

(60) Provisional application No. 60/577,167, filed on Jun. 7, 2004.

(51) Int. Cl.
*A61B 5/05* (2006.01)
(52) U.S. Cl. .......... 600/407; 600/462; 600/466
(58) Field of Classification Search ........ 600/423, 600/427, 433, 466, 471, 472, 478, 547, 114; 606/13
See application file for complete search history.

(56) References Cited

U.S. PATENT DOCUMENTS

| | | | | |
|---|---|---|---|---|
| 4,649,275 | A * | 3/1987 | Nelson et al. | 250/358.1 |
| 6,122,542 | A * | 9/2000 | Lee et al. | 600/427 |
| 6,146,377 | A * | 11/2000 | Lee et al. | 606/13 |
| 6,314,315 | B1 * | 11/2001 | Hung et al. | 600/547 |
| 2003/0055314 | A1 * | 3/2003 | Petitto et al. | 600/109 |
| 2003/0055315 | A1 * | 3/2003 | Gatto et al. | 600/114 |
| 2004/0167399 | A1 * | 8/2004 | Li | 600/430 |
| 2004/0220564 | A1 * | 11/2004 | Ho et al. | 606/47 |
| 2007/0025662 | A1 * | 2/2007 | Gugel | 385/39 |

\* cited by examiner

*Primary Examiner* — Tse Chen
*Assistant Examiner* — Joel F Brutus
(74) *Attorney, Agent, or Firm* — Ade & Company Inc; Michael R. Williams

(57) ABSTRACT

A method of scanning breast tissue involves inserting an imaging element into a breast via a carrier inserted into a breast duct. The imaging element may be for example a receiver, a transmitter or a mirror. A signal is transmitted between one imaging element within the breast duct and a second imaging element outside the breast.

5 Claims, 3 Drawing Sheets

SYSTEM AND MICRO-CATHETER DEVICES FOR MEDICAL IMAGING OF THE BREAST

PRIOR APPLICATION INFORMATION

This application claims the benefit of U.S. Provisional Patent Application 60/577,167, filed Jun. 7, 2004.

BACKGROUND OF THE INVENTION

Holey Fiber, also called Crystal Fiber, was first developed at the University of Bath in 1995 based on the work of Philip Russell. Unlike normal optical fiber which is solid throughout, holey fiber is fabricated with one or more continuous open channels running from one end to the other. These can be very small diameter channels, with diameters of 3 micrometers and less being possible today. Holey fiber may be made from glass or plastic. These channels have previously been filled with gas in an application to develop a high-power laser. Recently, holey fiber has been investigated for use in medical applications within the endoscope subject area, in which viewing of the interior of the body is the purpose. This work was done by Martijn van Eijkelenborg, Australian Photonics Cooperative Research Center, University of Sydney, Australia. A short paper on this topic is M. A. van Eijkelenborg, "Imaging with microstructured polymer fibre," Opt. Express 12, 342-346 (2004).

In this case the holey fiber is used for passing optical frequencies, there are optical frequencies traveling in both directions, and the application is viewing of the interior of the cavity. It is interesting to consider, however, whether holey fiber can be used for other medical purposes, such as a combined device in which both electromagnetic energy and physical objects are passed along the channels. This field of study would usually be called capillary optics or capillary devices, however a key difference between holey fiber (also sometimes called crystal fiber or photonic band-gap fiber) and capillary tubes is that the electromagnetic confinement ability of the holey fiber is much better than a capillary tube.

Holey fiber can be manufactured to (1) provide what are effectively multiple capillary tubes capable of passing liquids, gels, gasses and solid objects, while also (2) preserving the ability to carry and confine electromagnetic radiation either in optical, infrared, microwave or RF form, from one end to the other. The unique property of light guidance was recognized by Benabid, Knight and Russell ["Particle levitation and guidance in hollow-core photonic crystal fiber", F Benabid, J C Knight, P. St. J Russell, Optics Express 21 Oct. 2002 vol 10(21) 1195] as a key difference between holey, crystal, photonic bandgap fibers and their related capillary tubing cousins. Also, just as optical fiber can carry light, it can also carry microwaves or other electromagnetic radiation. It is also possible for different channels within the same holey fiber to be manufactured to guide different wavelengths.

How can these unique holey fiber properties be used to improve breast imaging for the purposes of breast disease analysis, breast cancer detection and treatment, and improvements in breast surgery? As well, what are the implications of this unique fiber family in the design of micro-catheters for other medical operations, such as intravascular inspection and treatment?

Breast imaging for the purposes of finding cancerous lesions is an important industry and technology area because breast cancer is a leading cause of death for female adults. Many methods have been tried in the industry, as reviewed in the book "Mammography and Beyond", as discussed at workshops such as Workshop on Alternatives to Mammography 2004 in Winnipeg, and as discussed within the relevant research literature such as TCRT (Technology in Cancer Research and Treatment), IEEE Medical Imaging, and other publications.

The methods that have been discussed include X-Ray imaging (film and full-field digital mammography), thermography (in which hotter local areas are indicative of increased blood flow, potentially indicating tumor growth), ultrasound imaging, MRI (Magnetic Resonance Imaging), optical and infrared imaging at various frequencies using various techniques, microwave and RF imaging at various frequencies using various techniques, PET imaging (in which injections occur to cause positron radiation), contrast enhanced imaging (in which breast ducts are insufflated with appropriate fluids or gases to allow increased contrast), SPECT imaging (in which photon emissions occurs, instead of positrons as in PET, but injections are again required), fluorescence techniques, etc. For most of these methods, the basic configuration is the same, in that the imaging reception and transmission equipment is external to the breast. Relatively new techniques, such as Optical coherence tomography and Photon Migration Spectroscopy, have been developed for imaging with ultrahigh resolution. Additional and newer detection methods use genetic markers for breast cancer. There has also been work on the visual inspection of the interior of the breast duct using ductoscopes, and work on the obtaining of nipple aspirate fluid and its evaluation. Additional interesting research work has occurred in the area of Bio-Mems designs ("A Bio-Mems Device for Separation of Breast Cancer Cells from Peripheral Whole Blood", Juan Feng, M.S.M.E. Thesis, Dept. of Mechanical Engineering, Louisiana State University, 2003-12-18).

In 2001, a report discussed the state of the art in catheter-based imaging. These authors indicated that Optical Coherence Tomography (OCT) was investigated, and that a catheter designed with an OCT capability was able to image approximately 0.5 mm around a porcine vein. Similarly, the inventor of the OCT technique (Fujimoto from MIT) discussed OCT imaging inside the body using a catheter based technique in 1999. These reports did not mention the use of in-duct detectors or transmitters being used with outside-the-breast transmitters or detectors.

Many patents have been filed in relation to breast imaging and breast cancer. In 1974, a method was outlined for aiding in the detection of breast cancer (U.S. Pat. No. 3,786,801) with the method being for the use of nipple aspirate fluid and methods to extract the fluid. In 1985, U.S. Pat. No. 4,556,057 discussed the use of an excimer laser, a light pipe, and the fluorescence of the cancer in detecting cancerous areas. The method of luminescence was used in U.S. Pat. No. 4,930,516, granted Jun. 5, 1990, entitled Method for detecting cancerous tissue using visible native luminescence.

U.S. Pat. No. 5,813,988 entitled "Time-resolved diffusion tomographic imaging in highly scattering turbid media", claims a method of measuring and converting a diffused optical signal through the breast into an image of the breast, such that breast cancer or other problems can be detected. In this case the authors are using a trans-illumination approach to the breast imaging problem, which is different than introducing an imaging receiver or transmitter into the breast itself.

Microwave methods related to breast cancer are discussed in U.S. Pat. Nos. 6,768,925; 6,421,550; 5,983,124; 5,779,635; 5,662,110. These patents discuss the use of microwave detection of tumours within the breast, discrimination methods between malignant and benign breast tumours, and treatment of breast cancer.

Optical methods for breast cancer detection, including detection of lesions and discrimination of cancerous and non-cancerous lesions via various techniques, have been discussed in U.S. Pat. No. 5,876,339.

Implantable illuminators for therapy of the breast have been outlined in U.S. Pat. No. 6,027,524. This patent mainly discusses the design of a "cup" for imaging uniformly near the nipple area, and then discusses the post-surgery implantation of a device. This patent discusses the treatment of post-surgical tissue using photodynamic therapy, with the photodynamic therapy delivered using a rigid or almost rigid "cup" around the breast. However, there is no teaching of inserting a ductascope into the nipple while the cup is in place.

U.S. Pat. No. 6,846,311 from Acueity, granted Jan. 25, 2005 and entitled "Method and apparatus for in VIVO treatment of mammary ducts by light induced fluorescence" claims a micro-catheter which will excite a given area, receive the fluorescence of the area, thereby determining whether cancerous cells are located there or not, and will then necrose the cancerous area through the delivery of a light source. In this case a ductal compound is introduced into the breast, the compound may be allowed to "sit" for 1 to 4 hours, and then the fluorescence method of breast cancer detection is used within the breast. This approach is completely different from the approach which is presented here, in which the receivers and transmitters are inside and outside the breast. There is also no concept of multiple receivers and transmitters inside and outside the breast.

U.S. Pat. No. 6,825,928 called Depth-resolved fluorescence instrument was invented by Liu, Ramanujam and Zhu with the patent granted Nov. 30, 2004. In this invention, they provide for a device to measure the fluorescence of a sample at various depths. The purpose of measuring this fluorescence was to detect changes in cells which indicated that cancerous growth might be starting. Within this patent they cited U.S. Pat. No. 6,014,204 entitled Multiple diameter fiber optic device and process of using the same.

Many other patents have been filed. None of those of which we are aware discuss the use of receivers and transmitters introduced into the breast duct for the purposes of receiving and/or transmitting to system elements outside of the breast. As well, none of the previous work discusses the unique abilities of holey fiber as applied to micro-catheter design.

In a review of mammary ductoscopy, which was accepted on 8 Oct. 2004 (Mammary Ductoscopy: current status and future prospects", K. Mokbel, P F Escobar and T Matsunaga, 8 Oct. 2004, The Journal of Cancer Surgery) there was no mention of imaging from inside to outside the breast or vice-versa and no mention of placing detectors or sources inside the breast for such a purpose. There was also no mention of the benefits of holey fiber for the design of the ductoscopes and endoscopes necessary to do this function. This paper reviewed the work of Dr. James Going, indicating that:

> There are three types of duct systems in the female breast, with type A being large ducts that drain the majority of the breast, type B being ducts that tapered to a minute lumen within 1 mm from the skin surface, and type C which were a minor duct population. (Other studies have found that duct sizes are typically 1-2 mm but often change during breast feeding and due to hormones).
> That the implication is that only type A ducts can be investigated by Mammary Ductoscopy
> That it is not known whether cancer occurs in all three types of ducts, or whether type A contains the majority of the cancer.

This paper also noted that nipple manipulation was required to access some of the ducts, and that the majority of the ducts were not so convoluted that ductoscopy would not work. This paper noted that it is believed that 85% of breast cancer occurs directly from the epithelial lining of the mammary ducts or lobules. This indicates that 15% of the non-duct based cancers must still be detected by methods which do not inspect the duct linings, and therefore it is necessary to have some method of imaging from inside to outside and outside to inside. As well, if not all ducts are available to mammary ductoscopy, it implies that some inspection of smaller ducts should occur from adjacent ductal passages that can be accessed.

On Sep. 1, 2004 ("Endoscopically Compatible Near-infrared Photon Migration Probe, C. Lubawy and N. Ramanujam, Optics Letters Vol 29(17) pp 2022-2024) there is a description of an endoscopically compatible near-infrared photon migration probe. In this case, the authors indicate that the probe can be used endoscopically or via biopsy needle, that it is 2.3 mm in diameter (which is too large for breast duct work), that it is specifically targeted at breast cancer work based on needle biopsy, and that it is designed to be used with the PMS (photon migration spectroscopy) technique. In this paper, the authors illustrate the potential to use a receiver and transmitter which is on the same platform or fiber. This paper does not discuss imaging from the inside to the outside, or imaging from the outside to the inside.

Within the field of in-duct breast imaging, it seems therefore that there are three general classifications of imaging systems, based on whether the imaging technology looks at the duct lining (Type 1), the duct locale (Type 2, approximately the area 0 to 10 mm around the duct using reflection of the illumination off of the surrounding tissue) or the whole breast (Type 3, which occurs when the entire breast from point of detector/transmission inside the breast to point of detector/transmission outside the breast is included, using transmission through the intervening tissue). For each of these general classifications, one can use optical, infrared, microwave, thermal, ultrasound, or other imaging technologies to obtain information.

Some of the Type 1 systems have been discussed in the literature. These are visual inspection of the breast duct lining, and is normally done via endoscopy using commonly available equipment. Pictures of breast ducts are available on the Acueity website. As well, some of the patents cited above have included optical and other imaging techniques as part of their endoscopic procedure.

The work by Fujimoto on catheters that provide OCT imaging, as well as the work of the Advance Imaging Catheter team of Lawrence Livermore, provide Type 1 and Type 2 imaging depending on the imaging depth that they can achieve. The other imaging catheters within the literature that use ultrasound also use Type 2 imaging, because they do not view from inside to outside the body. Type 2 imaging is also discussed within U.S. Pat. No. 6,825,928.

To the present time, we know of no study on in-breast-duct imaging that discusses Type 3 imaging.

Described herein are systems and ductoscope equipment necessary to allow receivers and transmitters to be placed within the breast, to communicate and signal to systems and detectors and transmitters outside of the breast, and thereby to generate an improved breast imaging system.

SUMMARY OF THE INVENTION

According to a first aspect of the invention, there is provided a device for breast imaging comprising:

a first imaging element within a carrier, said carrier being arranged for insertion into a breast duct;

a second imaging element arranged to be mounted onto a breast; and a control unit arranged to receive signals from at least one of the first imaging element or the second imaging element.

According to a second aspect of the invention, there is provided a method of scanning a portion of breast tissue suspected of containing a cancerous lesion, comprising:

providing a breast to be examined, said breast comprising breast tissue and a nipple;

inserting a carrier having a first imaging element inserted therein into a breast duct via the nipple of the breast;

positioning a second imaging element outside the breast tissue; and passing energy between the first imaging element and the second imaging element.

DESCRIPTION OF THE PREFERRED EMBODIMENTS

Figure 1:
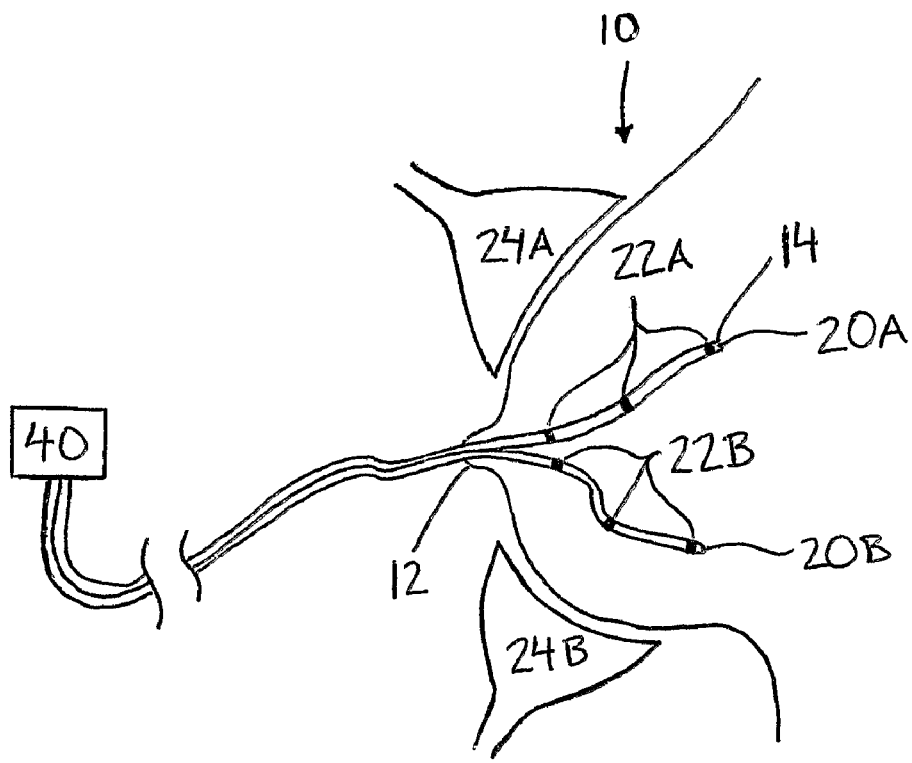
FIG. 1 is a schematic diagram of one embodiment of the invention, wherein a first carrier comprising one or more transmitters is inserted into a first breast duct and a second carrier comprising one or more receivers is inserted into a second breast duct.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference. As used herein, the terms "channel" and "lumen" are in some contexts used interchangeably as will be readily apparent to one of skill in the art.

Described herein is a method of scanning breast tissue wherein an imaging element is inserted within a breast via a carrier inserted into a breast duct within the breast for imaging the breast tissue located between the in-duct imaging element and an imaging element located outside of the breast. As will be appreciated by one of skill in the art, inserting an imaging element within the breast has significant advantages over traditional methods such as X-ray mammography which requires compression of the breast and trans-illumination of the breast as discussed herein. The imaging element may be for example a receiver, a transmitter or a mirror. As discussed below, in some embodiments, a signal is transmitted between a transmitter and a receiver, wherein at least one of the transmitter or the receiver is inserted within the breast for scanning by a carrier as discussed below while the other is positioned outside the breast. As a result of this arrangement, the two imaging elements are within close proximity of one another, that is, for example, within approximately 4 cm or within 3.5 cm or within 3 cm or within 2.5 cm or within 2 cm or within 1.5 cm or within 1.0 cm. As discussed below, because of this proximity, less energy is needed for scanning and better resolution and clarity is obtained due to less attenuation. The receiver(s) are connected either via the carrier or by wireless means to a control unit which receives and analyzes the data from the receiver(s). As discussed below, cancerous lesions attenuate or otherwise abnormally interact with emitted energy and will therefore produce an abnormality which is detected by the control unit, as discussed below. Thus, the instant method is arranged for analyzing breast tissue using either a transmitter or receiver within a breast duct.

It is further of note that as discussed herein, cancerous tissue is known to have different luminescent properties relative to healthy tissue. Furthermore, some specific frequencies or wavelengths wherein these differences are most pronounced are well-known and well-established in the art and may be used within the invention, as discussed below. Alternatively, other suitable wavelengths and/or frequencies may be utilized. That is, energy propagated through healthy tissue at a given frequency or wavelength will exit a tissue portion with a different profile than will energy at the same or similar frequency or wavelength propagated through tissue containing a cancerous lesion.

The transmitter transmits energy. The transmitter may be a single unit or may be an array comprising multiple transmitters. Each transmitter may be arranged to emit energy at more than one frequency or wavelength. In some embodiments, the wavelength or frequency is selected based on the specific interaction of energy at that wavelength or frequency with lesions. Furthermore, as discussed below, a wide variety of energies may be utilized within the invention, for example but by no means limited to optical, infra-red, microwave and RF.

The receiver receives energy from the transmitter. The receiver may be a single unit or may be an array comprising multiple receivers. Each receiver may be arranged to either record data received from the transmitter or may transmit the data to a control unit, for example, an analytical unit either by wireless transmission or via the carrier.

The carrier is arranged for insertion into a breast duct of the patient. As discussed below, the carrier may be a traditional ductascope as known in the art or may be a holey fiber scope, as discussed herein. As discussed above, the breast ducts are typically 1-2 mm in diameter, although it is important to note that the ducts are not linear and likely have highly variable diameters. Typical ductoscopes known in the art are approximately 0.4 mm. Optical fiber, including holey fiber, can be made with a core size of 0.01 mm, with channels as small as 0.003 mm, and in various other combinations of physical parameters. As discussed below, at least one transmitter and/or receiver is inserted into the carrier prior to insertion of the carrier into the breast duct. As will be evident from the dimensions of imaging elements discussed below, suitable imaging elements can be inserted into a carrier, for example, a ductoscope, having a diameter of about 0.4 mm to 1 mm or from 0.4 mm to 0.8 mm or from 0.4 to 0.6 mm. In alternative embodiments, the carrier may be composed of holey fiber and may comprise a plurality of channels as discussed herein and may have a total diameter of about 0.01 mm to 1 mm, of about 0.01 mm to 0.8 mm, of about 0.01 mm to 0.6 mm, of about 0.01 mm to 0.4 mm, of about 0.01 mm to 0.2 mm, of about 0.05 mm to 1 mm, of about 0.05 mm to 0.8 mm, of about 0.05 mm to 0.6 mm, of about 0.05 mm to 0.4 mm, of about 0.05 mm to 0.2 mm, of about 0.1 mm to 1 mm, of about 0.1 mm to 0.8 mm, of about 0.1 mm to 0.6 mm, of about 0.1 mm to 0.4 mm, or of about 0.1 mm to 0.2 mm.

Referring to the drawings, a breast 10 has a nipple 12 and one or more breast ducts 14.

As discussed herein, with reference to FIGS. 1-4, the carrier 20 has been inserted into a breast duct 14 via the nipple 12.

Figure 2:
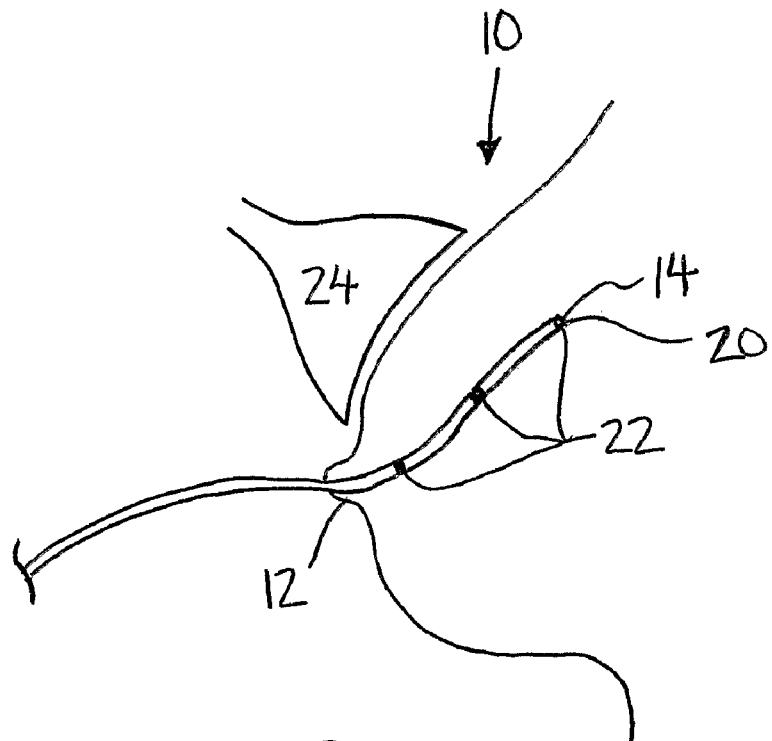
FIG. 2 is a schematic diagram of a further embodiment of the invention.
Figure 3:
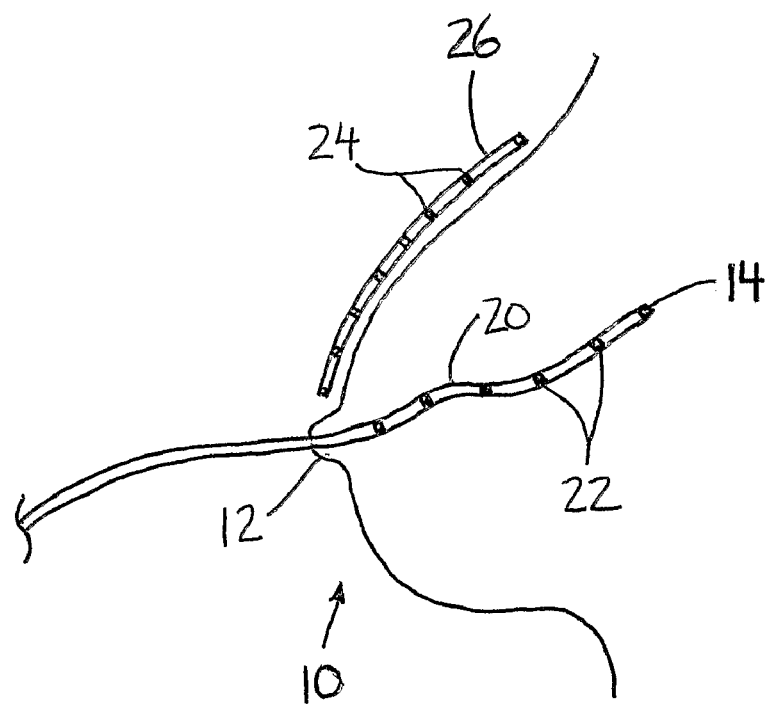
FIG. 3 is a schematic diagram of an embodiment of the invention wherein the external imaging elements are mounted in an array.

In the embodiment shown in FIG. 2, for example, the carrier 20 includes three interior imaging elements 22 within the carrier and an external imaging element 24. As discussed below, in some embodiments, the external imaging element 24 is a transmitter and the internal imaging elements 22 are receivers which receive energy from the transmitter and transmit this information to a control unit, either through a wire or other means or via wireless means. In other embodiments, the external imaging element 24 is a receiver and the internal imaging elements 22 are transmitters which emit energy which is collected by the transmitter, as discussed below. In yet other embodiments, the internal imaging element 22 is a mirror and the external imaging element 24 is a receiver, as discussed below. As discussed below, the carrier 10, the internal imaging element 22 and the external imaging element may be connected to a control unit which may analyze results from the receiver and/or regulate the operation of the internal imaging elements 22 and the external imaging elements 24 as discussed below.

Referring to FIG. 1, shown is the insertion of carriers in two breast ducts. As will be appreciated by one of skill in the art, in some embodiments, the carriers are inserted into the breast ducts simultaneously and the internal imaging elements 22A in the first carrier 20A are transmitters while the internal imaging elements 22B in the second carrier 20B are receivers. In this arrangement, the external imaging element 24A is a transmitter and the external imaging element 24B is a transmitter. As a result of this arrangement, breast tissue between the first carrier 20A and the second carrier 20B can also be analyzed as can the breast tissue between the carrier 20A and the external imaging element 24A and the breast tissue between the second carrier 20B and the external imaging element 24B. In other embodiments, internal imaging elements 22A and 22B may be transmitters and external imaging elements 24A and 24B may be receivers. In other embodiments, internal imaging elements 22A and 22B may be receivers and external imaging elements 24A and 24B may be transmitters.

One of the simplest examples for a transmitter method within the breast is to use mirrors at the distal end to reflect the signals that are injected at the proximal end. Micro-mirrors are very common within telecom and electronics applications, and their technology is well advanced. For example, as reported in Nov. 15, 2004 Optics Letters, it is possible to make a micro-mirror assembly of 3×3 mirrors, with each mirror being 0.16 mm×0.16 mm in size. This research is from the National University of Singapore, and is done by Zhou, Logeeswaran, Fook and Tay. (Line-Addressable Digital-Deflection Programmable Micromirror Array" Optics Letters, Volume 29, Issue 22, 2581-2583, November 2004. Research and development work in Colorado indicates that mirrors as small as 0.06 mm×0.06 mm are possible today, and that arrays of such mirrors can be fabricated. Mirrors and mirror assemblies such as this can also be used as receiver elements, in that they will reflect signals from outside the breast into the fiber, to be received at the proximal end. Whereas the micro-mirrors discussed above are usually controllable, in order to modify their angle of operation, simpler mirror end-caps are possible if a single fixed angle of usage is required. One such example would be a corner-cube reflector as discussed in "Optical communication link using micromachined corner cube reflector", Chu et al, Berkeley Sensor and Actuator Center, University of California at Berkeley. This paper is from 1997.

An example of a microwave element would be RFID chips. Currently, a small RFID chip which is 0.3 mm on a side is available from Hitachi. This chip includes an antenna, providing for power that can be read at a distance of 1 foot. Each chip costs on the order of $1 or less in large quantities, and the reader that is used with the chip costs approximately $1500. The company called SmartCode has produced a small RFID chip roughly 0.25 mm square. These chips operate at the 928 MHz range of RF frequency. These products are small enough to be passed down a holey fiber channel. These types of products would need to be suitably packaged in order to move down the channel, and will get smaller with time. Modifications of RFID design would be needed to develop an appropriate detector or transmitter. For optical imaging systems, endoscopes today use small LEDs or laser chips mounted on the end of the endoscope for illumination purposes.

For microwave and RF systems, the types of frequencies that have been discussed in the literature include: 6.5 GHz, 300 to 1000 MHz, and more generally frequencies up to 30 GHz.

Optical and near optical imaging uses near-infrared light, typically in the 650 nm to 1000 nm range. ("Using Near-Infrared Light to Detect Breast Cancer", Fantini et al. Optics and Photonics News, November 2003). Time-resolved optical mammography also uses 637 to 985 nm illumination ("Time-Resolved Optical Mammography between 637 and 985 nm: clinical study on the detection and identification of breast lesions", Taroni et al, Phys. Med. Biol. 50(2005) 1-20. Received 15 Mar. 2005).

In luminescence studies the excitation range discussed is generally 250 to 450 nm (which spans the ultraviolet and visible spectral range) and the emission maxima range is within 280 to 700 nm. The difference between the energies is because after absorption of a photon, some energy is lost due to non-radiative processes. The particular energy which is radiated, and the spectra distribution of the radiation, is indicative of the material which is radiating, allowing for identification of the presence of cancer cells.

The control system is arranged to receive data from the receiver(s), as discussed above. It is noted that in some embodiments, the control unit may use the data from the receiver(s) for real-time imaging of the breast tissue and/or may analyze the data from the receivers for abnormalities potentially caused by breast lesions, as discussed below. In some embodiments, the control unit may also be arranged to control the activation of transmitters as well as other parts of the system, as discussed herein.

Figure 4:
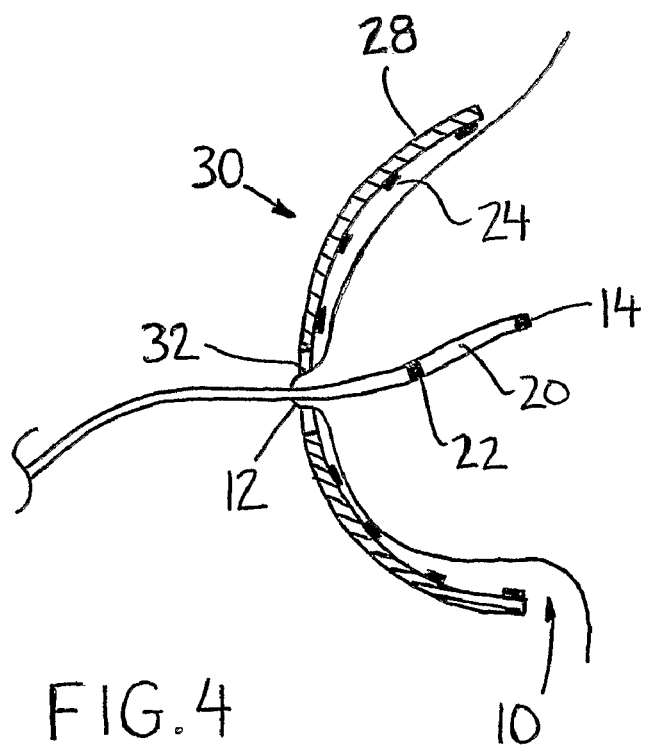
FIG. 4 is a schematic diagram of an embodiment of the invention wherein the external imaging elements are mounted to the inner surface of a cup which is mounted onto the breast of the patient.

As discussed herein, wherein a plurality of transmitters and/or receivers are utilized, the transmitters and/or the receivers may be arranged in an array, for example, a support having multiple transmitters or receivers mounted thereon, as shown in FIG. 4. Specifically, as can be seen in FIG. 4, the external imaging elements 24 are mounted to a support 26 which as discussed above can be repositioned on the breast 10 for scanning other portions of the breast 10. In a preferred embodiment, shown in FIG. 4, the external imaging elements 24 are arranged as an array and mounted onto an inner surface 28 of a cup 30 which is arranged to be fitted over a breast 10 such that the nipple 12 is exposed through an opening 32 in the cup 30 for accessing the nipple 12 as discussed above. In the embodiments wherein the transmitters and/or receivers are arranged in an array, the activation or utilization of these elements may be controlled individually or grouped according to location such that their activity can be regulated, thereby facilitating imaging.

In some embodiments, there is provided a system for breast imaging comprising: a first imaging element within a carrier, said carrier being arranged for insertion into a breast duct; a second imaging element arranged to be mounted onto a breast; and a control unit arranged to receive signals from at least one of the first imaging element or the second imaging element.

As discussed herein, the carrier may be a ductoscope or composed of holey fiber. The imaging elements may be receivers, transmitters or mirrors, as discussed below. The second imaging element may be a plurality of receivers or transmitters mounted onto a support for example in an array or the support may be a cup arranged to be fitted over a breast such that the nipple is exposed.

In other embodiments, there is provided a method of scanning a portion of breast tissue suspected of containing a cancerous lesion comprising: inserting a carrier having a first imaging element inserted therein into a breast duct; positioning a second imaging element outside the breast tissue; and passing energy between the first imaging element and the second imaging element.

As discussed herein, the energy passed is preferably at a frequency that is diagnostic for cancerous lesions, that is, at a frequency or wavelength wherein the interaction of cancerous tissue with that specific wavelength or frequency differs from the interaction between that wavelength or frequency and normal or healthy or noncancerous tissue. As discussed above, several of these frequencies and wavelengths are well-known in the art. Furthermore, it is noted that other such wavelengths and frequencies or combinations of wavelengths and frequencies can easily be determined through routine experimentation as well as through analyses such as multi-variate analysis and using wavelengths and frequencies selected from the ranges of wavelengths and frequencies discussed above.

It is of note that in some embodiments, the method may include repositioning the first imaging element and/or the second imaging element prior to passing energy between the two imaging elements again.

For use, the device and system may be arranged in a variety of ways and configurations, as discussed below.

For example, in one embodiment, the carrier has at least one receiver inserted therein and the system includes external transmitters which are placed on the surface of the breast. For example, there may be one transmitter, three transmitters or an array of transmitters, with each transmitter in the array being located at a discreet position relative the other transmitters. As will be appreciated by one of skill in the art, any suitable number of transmitters may be used and when mounted on an array will be arranged such that each transmitter emits energy to the receiver individually or distinctly. In some embodiments, the receiver may be at a fixed location in the carrier and the position of the carrier within the breast is modified by inserting or retracting the carrier. In other embodiments, there may be a plurality of receivers inserted at discreet locations within the carrier. These receivers may be separated by spacers, as discussed below. Alternatively, the receiver may be arranged to travel along the carrier, thereby effectively scanning the breast tissue while in motion. In these embodiments, the transmitter(s) emit energy into the breast which is received by the receiver(s). As will be appreciated by one of skill in the art, coordination of the activation of the transmitter(s) and recordation of data received from the receiver(s) provides increased sensitivity and therefore a clearer result.

In another embodiment, the carrier has at least one transmitter inserted therein and the system includes external receiver(s) which are placed on the surface of the breast. For example, there may be one receiver, three receivers or an array of receivers, with each receiver in the array being located at a discreet position relative the other receivers. As will be appreciated by one of skill in the art, any suitable number of receivers may be used. In some embodiments, the transmitter may be at a fixed location in the carrier and the position of the carrier within the breast is modified by inserting or retracting the carrier. In other embodiments, there may be a plurality of transmitters inserted at discreet locations within the carrier. Alternatively, the transmitter may be arranged to travel along the carrier, emitting energy to the receiver either continuously or at regular intervals, thereby effectively scanning the breast tissue while in motion. In these embodiments, the transmitter(s) emit energy into the breast which is received by the receiver(s). As will be appreciated by one of skill in the art, coordination of the activation of the transmitter(s) and recordation of data received from the receiver(s) provides a more accurate, more easily interpreted result.

In use, the carrier with the transmitter(s) or receiver(s) inserted therein is inserted into a breast duct and scanning is carried out, as discussed in the examples. As discussed herein, this procedure is carried out without compression of the breast, thereby increasing the comfort of the individual undergoing the procedure. As discussed above, because of the relatively short distance between the receiver and the transmitter, lower levels of energy can be used, thereby increasing safety, without sacrificing sensitivity.

The invention will now be described by way of examples. However, the invention is not limited to the examples and it is to be understood that the examples are for illustrative purposes.

According to a first example of the invention, there is provided a receiver introduced into the breast duct via a ductoscope, with the receiver attached at a distal end of the carrier or mounted within a distal end of the carrier, for example, the end of the carrier that is inserted into the breast. In this case, the patient may be lying down on a bed with one or both breasts hanging below the bed, or the patient may be in another position. The breast under study is gently held by a suitable apparatus, but is not under compression. The ductoscope or other carrier is inserted into the breast. As the ductoscope is inserted into the breast, periodically the insertion is halted while measurements are taken, as described above, that is, while communication between the imaging elements is occurring. In these embodiments, the carrier may include calibrations on an exterior surface thereof for monitoring and/or determining insertion depth. In this example, the transmitter is a transmission array with 8 transmission elements that provide signals that the receiver receives that is placed on the outer surface of the breast. In some embodiments, optical signals are used, however infrared, microwave or RF signals can also be used. Furthermore, it is also assumed that the receiver is an omnidirectional receiver in the plane of the ductoscope, such that the receiver does not necessarily receive any imaging signals along the axis of the fiber but receives all signals 90 degrees from the ductoscope axis. As discussed above, the receiver communicates with the control unit either through the ductoscope itself or via wireless methods. As discussed above, the receiver can thereby be synchronized, turned on and off, and powered using various means known in the art.

In use, the carrier is inserted into a breast duct such that the receiver is at a first receiver location, for example 2 cm. into the breast duct. As will be appreciated by one of skill in the art, the first step of the process is locating the receiver, followed by the generation of the imaging signals. The receiver location may be found by using three location signals, also in the optical domain at the appropriate frequency. These location signals may be generated using an optical laser. For locating, the laser is manipulated until the signal level received is at a maximum, and then the angle into the breast of the three measurements is used to calculate the position of the receiver. In other embodiments, more than three measurements can be used for redundancy and for accuracy. Using this method or similar means known in the art, the location of the receiver within the breast can be determined, and this information can be used by the control unit. It is of note that this will also provide the orientation of the receiver within the duct.

As discussed above, in some embodiments, the transmitters are arranged to emit a signal at more than one frequency, for example, at frequency f1, f2 and f3. These frequencies f1, f2 and f3 may be selected from the set of frequencies commonly used within optical mammography work at the current time, such as those studied by Paola Taroni and the Milan group working on optical mammography. In these embodiments, the transmitters are lasers as well, operating at optical frequency, may be pointed at the first receiver location. The receiver will measure 24 signals in total at the first receiver position, as there are 8 transmission positions and each position generates 3 frequencies.

The ductoscope is then moved to the second receiver position, for example, inserted an additional 2 cm. into the breast, and the series of 24 transmissions is repeated. As will be appreciated by one of skill in the art, other suitable insertion depths may be used, for example, 0.5 cm, 1 cm, 0.75 cm and the like, depending on several factors including but by no means limited to the number of receivers and transmitters utilized as well as the initial results obtained. This continues until the final receiving position is reached. This process therefore generates 24 received signal levels at each position (based on the simple assumption that a single signal level is recorded for each frequency-transmission location pair). Thus, if there are 6 receiving locations, there are therefore 144 signal readings in total are available. These signal readings have been achieved without breast compression, but like breast compression methods the amount of breast material between the transmission and reception point has been minimized through the manner in which the duct passageways have been used.

As discussed above, a breast lesion will be found if a sufficient number of measurement paths, that is, transmitter-to-receiver paths, cross over its location. As discussed above, the properties of energy emerging through a portion of breast tissue containing a cancerous tissue therein will have different properties compared to healthy tissue.

In the general case, one has received signals measured from transmission location d (for example) to reception location a (for example) as signal da. Signal da is going to be a function of: (1) the emitted signal strength of the laser, (2) the propagation behavior of the breast material, (3) the distance from transmitter to receiver, and (4) the angle "theta da" at which the transmitter and receiver are oriented. The distance between transmitter and receiver are known once the receiver position is calculated. The angle theta is not known for a specific path, but it is known that the receiver orientation will not change during the measurement time period. This information can be used to locate any areas having unusual breast properties. The emitted signal strength is known. Therefore, the primary uncertainty is the propagation behavior of the breast, which, as discussed above, is dependant on the presence of lesions which as discussed above have different properties compared to healthy tissue. Depending on which frequency is chosen, breast lesions will block or attenuate the signal to different degrees. One therefore obtains, as a result of these measurements, a matrix of 144 signal levels which may be used to triangulate the position of any lesions if present.

If an appropriate duct is available for navigation, the distance between transmitter and receiver will be short enough that all signals are received (ie. If the distance is too large, then no signal can be discerned above the noise floor of the surrounding breast tissue). As will be appreciated by one of skill in the art, signals travelling a greater distance will require greater initial power to overcome signal attenuation. Depending on the energy source, this may have consequences, such as increased risk of side effects. For example, X-ray mammography currently uses 3 cm compression widths to image. In the instant invention, because of the use of carriers within the breast ducts, the distances between imaging elements are generally less than 3 cm without compression meaning that the patient enjoys greater comfort and lower (safer) levels of energy can be utilized with greater sensitivity. The percentage of breast that has been inspected between these two lines will be near 100% as long as the spacing of transmitters and receivers is consistent with the beam collimation size and the amount of scatter that can be expected.

The receiver will receive signal levels during the imaging process, and as discussed above, will either have on-board memory to store the results or will communicate the results to a control unit, either by wireless means or by a cable within the carrier, as discussed above. After the imaging is done, the receiver is removed by retracting the carrier using means known in the art.

On completion of the process outlined above, one has imaged a given "slice" of breast, approximately the width of the transmitted beam collimation. In some embodiments, for example, wherein the transmitter array is small, the transmitter array is moved a certain or pre-determined distance around the breast and the imaging is repeated for the receiver locations described above. Alternatively, and more practically, the receiver locations should be adjusted as little as possible, and therefore the transmitter array should be moved completely around the breast for each of the 6 receiver locations. As discussed below, this may be accomplished by having a plurality of receivers inserted into the carrier so that the carrier is not moved during the analysis, while the position of the transmitter array is varied.

At the completion of such a process as described above, one would then have a slice by slice of the breast as analyzed from one breast duct. For example, if 50 radial slices were taken, and if the breast circumference were 100 mm, then one would have 2 mm between slices. Thus, a 2 mm collimated beam can be used to cover the entire breast. As such, lesions of similar size as the beam used above would be detected with this method. As will be appreciated by one of skill in the art, it is known that early detection of cancerous tissue generally results in more successful treatment.

In an alternative embodiment, the transmitter array or receiver array is mounted onto an inner surface of a cup-like structure which is arranged to be placed over the entire breast such that only the nipple protruding. As will be appreciated by one of skill in the art, in this arrangement, the breast ducts are still accessible to the carrier and the array is in a fixed position so that the time required to do the imaging is minimized. In this case, some of the transmission elements would be designated as being used to find the location of the receiver, and then all of the transmission elements would orient themselves automatically at the receiver and record image data accordingly.

In some embodiments, in order to gain additional accuracy, an alternative breast duct can be examined as discussed above. Again, the ductoscope would be inserted, imaging would occur, received signal levels would be measured, and the information would be transmitted to the control unit to determine the possible presence of lesions, as discussed above.

It is of note that the use of a different breast duct makes another set of data available, thereby improving the accuracy of the image of the breast. In a preferred embodiment, a breast duct that is most distant from previous ducts is selected in order to get a suitably different view. Therefore, in the process above, one generates multiple paths from multiple transmitter and receivers locations, imaging the entire breast as received within one breast duct passageway, and then another breast duct is selected and used for analysis, thereby improving the imaging accuracy.

It is of note that in the example above, for illustrative purposes, the process was simplified somewhat in a variety of ways. For example, a single receiver was imagined to be connected to the tip of the ductoscope. In reality, the ductoscope can be designed with multiple receivers to reduce the time required to record the imaging, as discussed above.

As discussed above alternative methods of usage for this system include using more than one receiver within the breast, placing one or more signal transmitter(s) in the breast instead of the receiver or receivers, or placing a population of one or more receivers and one or more transmitters in the breast. As discussed above, the transmitters do not necessarily need to be lasers, and do not necessarily need to be focused at a specific receiver location in order for the system to function.

For example, when doing near optical imaging, in place of lasers one can use light-emitting diodes. Light-emitting diodes have been used previously by researchers in near optical imaging of the breast. If the light source that is used for illumination is not directed or focused at the receiver/detector, this will modify the amount of light that is received by the detector but will not change the basic function of the equipment. If the imaging is done using microwave or RF techniques, the amount of focusing that can be done is less than that available using optical techniques, however the calculations required for antenna patterns are in the same spirit as those for optical detector and transmitter patterns. In the case of ultrasound imaging, typically arrays of elements are used, with the output of the array being a beam directed in a certain angle and direction. Depending on the number of elements, their size, and the array size, one has differences in the level of directivity of the beam. These differences in the beam parameters do not alter the basic workings of the system.

In other embodiments where a set of transmitters is introduced into the breast via a ductoscope, the procedure described above is substantially repeated but the transmitters are inside the ductoscope inside the breast, and the apparatus around the breast has receivers that receive the transmitted signals.

In the case where transmitters are introduced into the breast, it is necessary to ensure that signal levels are low enough that near-field effects (in the case of microwave and RF systems) do not cause damage to the near tissue. As well, for optical and infrared systems, the power must be kept below any damage level. For these EM methods, there is no ionizing radiation, and therefore no dosage problem, and therefore a much longer imaging time with greater accuracy and precision is possible.

As discussed above, existing imaging technologies can be used, for example using optical, infrared, near infrared, microwave, RF, ultrasound, X-ray and other imaging technologies. As discussed herein, all of these techniques are improved through the use of in-breast receivers and transmitters.

In some embodiments, the carrier is a unique micro-ductoscope, for example, one which is small enough to penetrate deeply into the ducts, but which can still carry receivers and/or transmitters.

In these embodiments, the carrier comprises a length of holey fiber having at least one continuous channel extending through the length thereof, wherein the holey fiber is arranged to accept a radiation transmitter or receiver therein.

In these embodiments, the system is provided with a holey fiber based micro-catheter design, with the design allowing gases, fluids and optical or EM energy to be passed down the same channel, which then allows the gas or fluid to be heated or excited using means known in the art, thereby causing an increase in temperature of the gas or fluid or causing the gas or fluid to radiate or otherwise emit a detectable signal. This allows a single-channel micro-catheter to provide both object and electromagnetic passage, which is an improvement on previous designs. The improvement comes from the potential to reduce the diameter required for the micro-catheter, meaning that the carrier is more comfortably inserted into the patient. As well, a smaller catheter can probe smaller ducts and passages within the body. For usage within the breast duct system, the smaller ductoscope allows a more thorough inspection of the breast duct system, because the breast ducts become smaller and smaller as they branch away from the nipple. Also, a smaller diameter ductoscope has a tighter bend radius. As discussed above, the breast ducts are not linear and do not necessarily have uniform diameters. As such, a carrier with a smaller diameter is more easily maneuverable within the duct and can also travel a greater distance up the duct which in some embodiments and circumstances may be advantageous.

In other embodiments, the carrier is a holey fiber with two channels, with these two channels being connected at the distal end (end inserted into the patient) such that an object can be moved along a channel by pressure being applied to either end of the channel. Essentially, this is like a single channel; however it is fabricated as a two channel holey fiber and then a "cap" is attached at the one end to allow the channels to be connected. In this case, pressure can be applied to the two proximal channel ends so that the object inside the channel can be moved into and out of the patient's breast duct. During this process, optical, infrared, Radio Frequency, Microwave or other wavelengths can be guided down the channel, and the wavelengths can bounce off of the object in order to illuminate the breast in the region surrounding the current position of the object. For example, the object may be a mirror assembly, which allows the wavelengths to bounce off of the mirror so that receiving systems outside the breast can receive the signal. The object can then be moved and the process repeated so that the wavelength will be received from the receivers again, and in this way an image of the breast can be obtained from the inside to the outside. Alternatively, the object may be a diffuse radiator, that is, an object that radiates in substantially all directions equally in which case many receivers may receive the point source image. Alternatively, the object may be an integrated circuit object, which receives the wavelength, converts the wavelength into power (as RFID chips do) and then radiates a signal. All of these options for the object are equivalent, in that pressure is used to move the object and the object illuminates the breast from that region.

Figure 5:
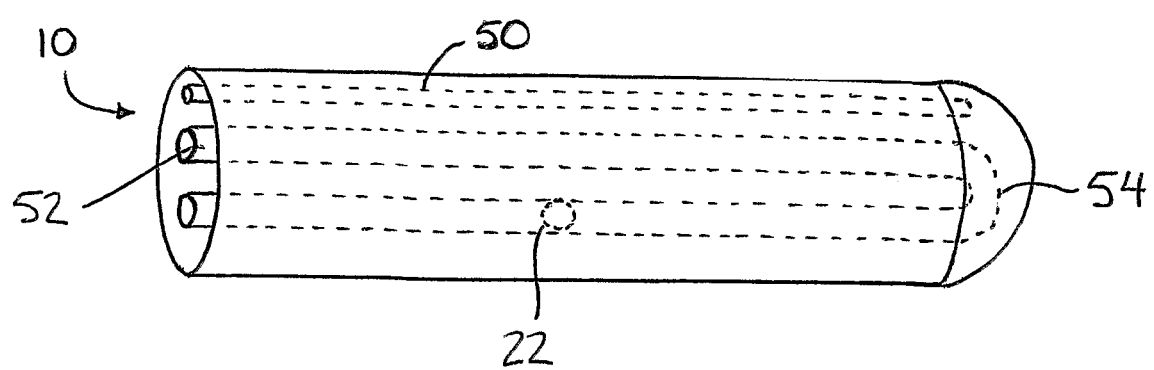
FIG. 5 is a schematic diagram of a carrier having a U-shaped channel for transmitting an imaging element to the end of the carrier and back.

In some embodiments, the carrier may include a pressure management and monitoring system for regulating movement of the imaging element along the carrier in those embodiments wherein the imaging element is mobile. For example, in these embodiments, the pressure management and monitoring system may be arranged such that a specific amount of pressure is produced in response to a specific stimulus and this amount of pressure is sufficient to move the imaging element a pre-determined distance along the carrier. In some embodiments, the carrier may have an open end such that the imaging element may be pushed along the carrier by applied pressure and then be effectively ejected from the carrier and into the duct for imaging therein. The imaging element may then be removed by flushing the duct once imaging is completed. Within the holey-fiber ductoscope are objects, either liquid, solid or gas, that are being passed into the breast. In other embodiments, at the end of the ductoscope is a termination, meaning that the ductoscope is not necessarily entirely open for all procedures. For example as shown in FIG. 5, the carrier 10 comprises a channel 50 which has an opening through the carrier for applying gases or fluids or other elements to the breast duct and a transport channel 52 which has the internal imaging element 22 inserted therein and has a U-shaped portion 54. In use, applied pressure directs the internal imaging element 22 to move from a first end of the transport channel 52, along the U-shaped portion 54, to the second end of the transport channel 52. The insufflation liquids and gases may be applied by a separate channel within the holey fiber ductascope.

As discussed above, the use of multiple receivers and transmitters decreases the time needed for scanning the entire breast and also increases the sensitivity and reliability of the method. For example, multiple receivers allow simultaneous signal reading and also increase reliability. Furthermore, the use of transmitters capable of emitting energy, for example, electromagnetic or ultrasound, at multiple frequencies also increases the utility of the system.

As discussed herein, in some embodiments, some of the receivers and transmitters are inserted in the breast via the carrier. These in-breast components of the system enter through the nipple using known methods of ductoscopy, as discussed above. By including external receivers and external transmitters, multiple paths between individual transmitters and receivers can be obtained, leading to a more accurate view of the portions of the breast between the transmitter and receiver pairs. As discussed above, the control unit can analyze the data from these pairs and locate the source of any abnormalities through triangulation of the signals.

In yet other embodiments, the breast could be imaged by providing a first carrier having at least one imaging element inserted therein inserted into a first breast duct and a second carrier having at least one imaging element inserted therein into a second breast duct proximal to the first such that energy can be passed between the two imaging elements for example for analyzing internal breast tissue. In these embodiments, each carrier may contain at least one receiver and one transmitter for communication with the corresponding receiver and transmitter in the other carrier. The presence of a receiver within each carrier also means that the location of each imaging element within the carrier can be determined using a locator as discussed above.

As discussed above, in other embodiments, the imaging element is a reflecting mechanism, for example a mirror, and all signal reception is performed outside of the breast. This system is suitable for those cases where no in-breast powering is allowed or desired.

As discussed herein, in some embodiments, there is provided a single channel holey fiber based catheter, having a small inner diameter and an open end, that allows for passage of electromagnetic or acoustic frequency or which allows for small objects to be passed and which also allows for simultaneous transmission of object and EMA (Electromagnetic and Acoustic).

In some embodiments, the imaging element is a reflective object such as a mirror that is pushed and pulled along the carrier via pressure, and electromagnetic energy is direct along the carrier. The energy bounces off of the object, which may be a mirror or suitably reflective surface, and illuminates that area of the breast. The illumination is then picked up by external receivers and the signal is analyzed. In this case, no active powering is required for inside the breast, allowing for a safer breast imaging procedure.

In other embodiments, there is provided a double channel carrier with a lens End Cap. The double carrier is used to illuminate the interior of the duct with a first wavelength, and then a second wavelength propagates down the catheter to be received and analyzed. This method is useful when the luminescence properties of the duct are being investigated. As discussed above, cancerous cells typically have different luminescent properties. In this case, the second channel is designed to propagate only the band of frequencies characteristic of cancer, which means that sensitivity is improved over previous designs. Also note that the external receivers and transmitters are not used in this case.

In other embodiments, there is provided a multi-channel system in which some of the channels are held in reserve for redundancy reasons in order to increase reliability. Specifically, some channels may become blocked or plugged for example due to problems with the imaging element, due to plugging of the carrier by duct fluid or insufflation fluids or the like. In these instances, it would be useful to have a second channel for continuing the procedure.

As discussed above, the imaging element may be an integrated circuit, such as an RFID, or MEMS device, which can be powered and turned on via electromagnetic energy such as optical frequencies. The object is turned on and is used for receiving and transmitting.

In yet other embodiments, there is provided a thermal mapping ductoscope, in which a thermal mapping disk that receives and records infrared emissions from the breast lining is moved down the inside of the ductoscope via pressure. This is useful in those cases where the duct lining is being inspected for temperature differences that arise from the increased blood flow that is associated with cancer. Notice that the ductoscope itself does not necessarily need to move, as the thermal imaging can be done through the side of the ductoscope if suitable plastic is used for the manufacturing process.

As discussed above, in some embodiments, there is provided an imaging element that slowly slides from one end of the carrier to the other while radiating, thereby providing a scanning motion for the receivers, which then allows the receivers to have a more accurate representation of the intervening tissue. In this case, the transmitter can be turned "on" throughout the sliding process, and the receivers can "strobe" the result. The scanning process will be slow enough that Doppler effects will not occur.

In other embodiments, the carrier includes an end cap that is held in place by the reduced pressure of the carrier, which also slightly deforms the end cap and reduces its size. The carrier is then inserted into the breast, the pressure returns to normal, and the end cap is left in the breast at the location where the pressure was released. This is done for treatment reasons. It is well studied that Brachytherapy can be done with radioactive seeds, and this approach allows the seeds to be placed at a given location. In concert with this leaving of the end cap, one must image the breast using appropriate technology to know where the end cap should be left. The end cap in this case has a special design allowing one channel to remain open, such that pressure can be used to allow removal of the device from the breast.

In another embodiment, there is provided a microcatheter design using holey fiber with a functioning end-cap, which allows a proximal system to provide power and control signaling over the holey fiber channel to the distal end. The distal end of the fiber is terminated with a functioning end-cap that uses gates, integrated circuits, MEMS devices and/or microrobotic systems that are powered and controlled for example using optical or other electromagnetic means by the proximal system, meaning that in these embodiments, no wires are needed. In this design, no distal end powering system is needed, which minimizes the long-term power requirements and simplifies the design. In this way, the smallest catheter design possible can be achieved. Along the holey fiber channel can be passed liquids at the same time as the EM power and control radiation is being passed down the channel, provided that the dielectric constants involved in the liquid-fiber interface do not significantly alter the EM guiding properties of the holey fiber. This design simplifies micro-catheter designs, in that local power does not have to be resident with the end device, and that a wire connection does not have to be maintained from the distal to the proximal end. This design also allows for a single small channel, guiding both liquids and EM radiation, to be used to squirt or insufllate with a high degree of sensitivity. This micro-catheter design can be used in the body in various ducts and orifices, such as penile, breast, esophagial, etc, and can also be used in non-medical applications.

While the preferred embodiments of the invention have been described above, it will be recognized and understood that various modifications may be made therein, and the appended claims are intended to cover all such modifications which may fall within the spirit and scope of the invention.

The invention claimed is:

1. A device for analyzing breast tissue for cancerous lesions comprising:
    an inserted transmitter or receiver, said inserted transmitter or receiver being inserted within a carrier, said carrier having an axis, said carrier being arranged for insertion into a breast duct within an uncompressed breast via the nipple of the breast, said inserted transmitter or receiver being inserted within the carrier such that the inserted transmitter is arranged to transmit energy at 90 degrees from the axis of the carrier or the inserted receiver is arranged to receive energy at 90 degrees from the axis of the carrier;
    a corresponding external receiver or transmitter arranged to be mounted onto the uncompressed breast outside of the uncompressed breast, wherein the external receiver is arranged to receive energy from the internal transmitter or the internal receiver is arranged to receive energy from the external transmitter after said energy propagates through breast tissue located between said inserted transmitter or receiver and said corresponding external receiver or transmitter; and
    a control unit arranged to receive data from the external receiver or the inserted receiver, said data relating to attenuation of energy emitted by said inserted transmitter or external transmitter to said external receiver or internal receiver respectively by passing through said breast tissue, said control unit being further arranged to analyze said data for an abnormal energy profile by comparison with a profile of energy propagated through healthy tissue, an abnormal energy profile indicating that said breast tissue contains a lesion.

2. The device according to claim 1 wherein the carrier is a holey fiber scope.

3. A device for analyzing breast tissue for cancerous lesions comprising:
    a first transmitter or receiver inserted within a first carrier, said first carrier having an axis, said carrier being arranged for insertion into a breast duct within an uncompressed breast via the nipple of the breast, said first transmitter or receiver being inserted within the carrier such that the first transmitter is arranged to transmit energy at 90 degrees from the axis of the first carrier or the first receiver is arranged to receive energy at 90 degrees from the axis of the first carrier;
    a second corresponding receiver or transmitter inserted within a second carrier, said second carrier having an axis, said second carrier being arranged for insertion into a breast duct within an uncompressed breast via the nipple of the breast, said second corresponding receiver or transmitter being inserted within the carrier such that the second transmitter is arranged to transmit energy at 90 degrees from the axis of the second carrier to the first receiver in the first carrier or the second receiver is arranged to receive a signal at 90 degrees from the axis of the second carrier from the first transmitter such that energy is propagated through breast tissue between the first carrier and the second carrier; and
    a control unit arranged to receive data from the first receiver or the second receiver, said data relating to attenuation of energy emitted by said second transmitter to said first receiver or by said first transmitter to said second receiver through said breast tissue, said control unit being further attanfed to analyze said data for an abnormal energy profile by comparison with a profile of energy propagated through healthy tissue, an abnormal energy profile indicating that said breast tissue contains a lesion.

4. The device according to claim 3 wherein the first carrier is a holey fiber scope.

5. The device according to claim 3 wherein the second carrier is a holey fiber scope.

* * * * *